United States Patent [19]

Uchida et al.

[11] Patent Number: 6,159,281
[45] Date of Patent: Dec. 12, 2000

[54] DETERIORATION PREVENTIVE FOR CONCRETE OR MORTAR AND METHOD FOR PREVENTING DETERIORATION OF CONCRETE OR MORTAR

[75] Inventors: Hiromi Uchida; Toshio Enokida; Reiko Tanaka; Michiko Tamano, all of Chuo-ku, Japan

[73] Assignee: Toyo Ink Manufacturing Co., Ltd., Japan

[21] Appl. No.: 09/117,816

[22] PCT Filed: Feb. 13, 1997

[86] PCT No.: PCT/JP97/00370

§ 371 Date: Aug. 10, 1998

§ 102(e) Date: Aug. 10, 1998

[87] PCT Pub. No.: WO97/30005

PCT Pub. Date: Aug. 21, 1997

[30] Foreign Application Priority Data

Feb. 13, 1996 [JP] Japan .................................. 8-024940
Oct. 7, 1996 [JP] Japan .................................. 8-265710

[51] Int. Cl.[7] .......................... A01N 55/02; C04B 24/12; C04B 103/67
[52] U.S. Cl. ....................... 106/823; 106/18.32; 106/727; 106/808; 524/183; 524/185
[58] Field of Search ..................... 106/727, 808, 106/823, 18.32; 524/185, 183

[56] References Cited

U.S. PATENT DOCUMENTS 5,435,846  7/1995  Tatematsu et al. .................... 106/813

FOREIGN PATENT DOCUMENTS

| 956 770 | 11/1999 | European Pat. Off. . |
|---|---|---|
| 63-16072 | 1/1988 | Japan . |
| 64-55493 | 3/1989 | Japan . |
| 2-265708 | 10/1990 | Japan . |
| 4-77338 | 3/1992 | Japan . |
| 4-149053 | 5/1992 | Japan . |
| 6-16460 | 1/1994 | Japan . |
| 6-16461 | 1/1994 | Japan . |
| 7-34002 | 2/1995 | Japan . |
| 7-70561 | 3/1995 | Japan . |
| 10-316461 | 12/1998 | Japan . |
| 10-316462 | 12/1998 | Japan . |
| 11-49542 | 2/1999 | Japan . |
| 11-61000 | 3/1999 | Japan . |

*Primary Examiner*—Anthony Green
*Attorney, Agent, or Firm*—Parkhurst & Wendel, L.L.P

[57] ABSTRACT

The present invention provides a deterioration inhibitor for concrete or mortar which does not pollute water and which, in a small amount, can prevent the deterioration of concrete or mortar due to sulfur oxidizing bacteria for a long time, and also provides a method of inhibiting the deterioration of concrete or mortar which uses the deterioration inhibitor. A phthalocyanine compound is an effective component of the deterioration inhibitor for concrete or mortar. In the method of inhibiting the deterioration of concrete or mortar, the phthalocyanine compound is added to concrete or mortar.

12 Claims, No Drawings

DETERIORATION PREVENTIVE FOR CONCRETE OR MORTAR AND METHOD FOR PREVENTING DETERIORATION OF CONCRETE OR MORTAR

TECHNICAL FIELD

The present invention relates to a deterioration inhibitor for concrete or mortar which inhibits and/or kills sulfur oxidizing bacteria and to a method of inhibiting the deterioration of concrete or mortar which uses the deterioration inhibitor. More particularly, the present invention relates to a deterioration inhibitor for concrete or mortar and to a method of inhibiting the deterioration of concrete or mortar which are preferably used for concrete or mortar structures in sewerage systems or the like.

BACKGROUND ART

In recent years, deterioration of concrete structures in sewerage systems or the like in Japan has been reported frequently. Deterioration occurs not only in Japan but also in other countries and has been reported in Australia, Egypt, South Africa, the U.S., and the like. Because it costs a large amount of money to build sewerage systems or the like, it is important to take appropriate measures against the deterioration of concrete so as to enable the system effectively to function over a long time.

It is known that the deterioration of concrete is caused by two types of microorganisms, i.e., sulfate reducing bacteria and sulfur oxidizing bacteria such as the genus Thiobacillus or the like. In the process of the deterioration of concrete by these microorganisms, firstly, sulfate in sewage (normally, the concentration of sulfate in sewage is within the range of 20 to 40 mg/l) is reduced by the sulfate reducing bacteria under anaerobic conditions and hydrogen sulfide is thereby generated. Next, the hydrogen sulfide is absorbed by water on the concrete wall surface and is oxidized by sulfur oxidizing bacteria under aerobic conditions. Sulfuric acid is thereby generated. Calcium in the concrete is changed to calcium sulfate (plaster) by the generated sulfuric acid. In this way, the concrete becomes fragile (deteriorates).

Among the aforementioned two types of microorganisms, the sulfur oxidizing bacteria is considered to be the main cause of the deterioration of concrete. Various methods have been proposed for inhibiting the change of hydrogen sulfide to sulfuric acid by the sulfur oxidizing bacteria.

One of these methods is a method of reducing the concentration of hydrogen sulfide which is a substrate for sulfur oxidizing bacteria. For example, methods are known in which air or oxygen is injected into sewage to oxidize hydrogen sulfide before the hydrogen sulfide is absorbed by water on the concrete wall surface, and to suppress the activity of the anaerobic sulfate reducing bacteria so that the generation of hydrogen sulfide is reduced. Among these methods, the method of injecting air into the sewage is a relatively simple method. However, in this method, the injected air may affect the equilibrium between the gas and liquid of the hydrogen sulfide such that the amount of hydrogen sulfide diffused in the air is larger than that in a case in which air is not injected. Further, hydrogen sulfide can be oxidized more effectively in the method of injecting oxygen into the sewage than in the method of injecting air. However, there is a drawback in that the cost of the method is high.

Another inhibiting method is a method of adding a large amount of chlorine, hydrogen peroxide, potassium permanganate, or a metallic salt whose metal is iron, zinc, lead, copper, or the like into sewage so that the hydrogen sulfide within the sewage bonds therewith. Further, Japanese Patent Application Laid-Open (JP-A) No. 7-70561 discloses a method of inhibiting the deterioration of concrete in which a water-soluble quinone derivative is added into sewage to oxidize hydrogen sulfide and to suppress the activity of the anaerobic sulfate reducing bacteria. However, since the material added into the sewage disappears as it flows, these methods are not effective and are expensive.

Moreover, a method of inhibiting the deterioration of concrete is known in which sulfur oxidizing bacteria is killed by mixing an antibacterial agent, which is an organic compound, with concrete. However, the antibacterial agent may generate pinholes or cracks in the concrete and may reduce the durability of the concrete. Further, at present, the use of Na—PCP (sodium pentachlorophenol) having a strong antibacterial action is prohibited.

Further, it is known that the growth of sulfur oxidizing bacteria is inhibited by a metal ion. JP-A No. 4-149053 discloses a method of inhibiting the deterioration of concrete in which a metal (e.g., copper, nickel, tin, lead or the like which is difficult to dissolve in water and is soluble in sulfuric acid) or the oxide of such a metal is added to concrete. In this method, metal ion is eluted from the metal and/or the metal oxide by sulfuric acid generated by sulfur oxidizing bacteria and inhibits and/or kills the sulfur oxidizing bacteria. However, in this method, because a metal having high solubility in sulfuric acid, or a metallic oxide having high solubility in sulfuric acid, or a mixture thereof is used, in order to prevent the deterioration of concrete over a long time, a large amount of metal or the like must be used. Further, since the heavy metal ion of nickel, tin, lead or the like is eluted into the sewage, water pollution may be caused by these metals.

Furthermore, JP-A No. 6-16460 and JP-A No. 6-16461 disclose methods of inhibiting the deterioration of concrete in which a metal complex such as nickelocene or nickeldimethylglyoxime is added to concrete. However, these metal complexes are carcinogenic and cause problems in terms of safety.

Several methods which use a material having resistance to sulfuric acid have also been proposed as methods of inhibiting the deterioration of concrete. For example, JP-A No. 63-16072 and JP-A No. 2-265708 disclose methods of protecting concrete by the lining of an epoxy resin, a polyester resin, or the like. Moreover, JP-A No. 1-55493 discloses a method of protecting concrete by the lining of a glass material.

However, in these methods, the construction cost is high, and since the lined material is peeled through pinholes, the life of concrete is short. Therefore, in order to maintain the effect of inhibiting deterioration, it is necessary to recoat the concrete periodically. The operation of the sewerage system or the like has to be stopped for a long time each time the concrete is coated.

Still further, a method in which concrete having excellent acid resistance and sulfate resistance is obtained by using slag cement or the like having a high percentage content of sulfate is also known. However, the strength of this slag cement is poor and the deterioration of the obtained concrete due to sulfuric acid cannot be completely prevented.

DISCLOSURE OF THE INVENTION

An object of the present invention is to provide a deterioration inhibitor for concrete or mortar which can effectively inhibit the deterioration of concrete or mortar for a long time and to provide a method of inhibiting the deterioration of concrete or mortar which uses the inhibitor.

The present invention provides a deterioration inhibitor for concrete or mortar in which a phthalocyanine compound is an effective component.

Further, the present invention provides a method of inhibiting the deterioration of concrete or mortar in which a phthalocyanine compound is added to concrete or mortar.

Sulfur oxidizing bacteria exist in sewage or the like and cause the deterioration of concrete or mortar. Several enzymes which relate to the oxidation-reduction of sulfur such as sulfideoxidase, sulfurdioxidase, or the like exist within a cell of the sulfur oxidizing bacteria, and sulfuric acid is generated due to the interaction of these enzymes (Koizumi, "Physiological Ecology and Biotechnology of Sulfur Oxidizing Bacteria", IRRIGATION WATER AND WASTE WATER, Vol. 31, page 307, 1989). Further, the sulfur oxidizing bacteria have the ecological characteristic in that a solid material such as a sulfur particle or the like can be a substrate. As a result, a phthalocyanine compound contained in concrete or mortar can be easily introduced into a cell of the sulfur oxidizing bacteria. The phthalocyanine compound which has been introduced into the cell of the sulfur oxidizing bacteria can inhibit and/or kill the sulfur oxidizing bacteria by inhibiting enzyme reaction within the cell of the sulfur oxidizing bacteria.

Further, in the deterioration inhibitor of the present invention, the component of the inhibitor is not eluted into sulfuric acid, unlike the above-described deterioration inhibitors which contain a metal or metallic oxide. Accordingly, a small amount of phthalocyanine compound can maintain the effect of inhibiting the deterioration of concrete over a long time. Furthermore, even if the above-described phthalocyanine compound is a metal phthalocyanine or a metal phthalocyanine derivative, the amount of metal ion eluted by the sulfuric acid is extremely small. Thus, water is not polluted.

Moreover, compared to the aforementioned metal or metallic oxide, the phthalocyanine compound is easily dispersed within a polymeric component included in a blending agent for concrete or mortar. Consequently, the phthalocyanine compound does not aggregate and precipitate in the blending agent, and a concrete or mortar in which a phthalocyanine compound is dispersed uniformly can be prepared. As a result, the effect of preventing deterioration can be manifested throughout the entire concrete or mortar.

BEST MODE FOR CARRYING OUT THE INVENTION

In the present invention, a phthalocyanine compound is a compound which has a phthalocyanine skeleton. More specifically, the phthalocyanine compound is a metal phthalocyanine, a metal-free phthalocyanine, and derivatives thereof.

The metal phthalocyanine used in the present invention is a compound in which a metallic atom is coordinated at a phthalocyanine skeleton which does not have a substituent. The metal phthalocyanine derivative is a compound which has a substituted atom other than a hydrogen atom or a substituent bonded to a benzene ring within a metal phthalocyanine molecule.

Further, the metal-free phthalocyanine used in the present invention is phthalocyanine ($H_2Pc$) in which two hydrogen atoms are coordinated at the center of the phthalocyanine skeleton. The metal-free phthalocyanine derivative is a compound which has a substituted atom other than a hydrogen atom or a substituent bonded to a benzene ring within a metal-free phthalocyanine molecule.

In the present invention, a phthalocyanine compound which is not soluble in water is preferably used.

Concrete examples of the substituted atom other than a hydrogen atom or the substituent in the metal phthalocyanine derivative and the metal-free phthalocyanine derivative include: halogen atoms such as fluorine, chlorine, bromine, and iodine; substituted or non-substituted alkyl groups such as methyl group, ethyl group, propyl group, butyl group, sec-butyl group, tert-butyl group, pentyl group, hexyl group, heptyl group, octyl group, stearyl group, trichloromethyl group, trifluoromethyl group, cyclopropyl group, cyclohexyl group, 1,3-cyclohexadienyl group, 2-cyclopentene-1-yl group, and 2,4-cyclopentadiene-1-ylidenyl group; substituted or non-substituted alkoxy groups such as methoxy group, ethoxy group, propoxy group, n-butoxy group, sec-butoxy group, tert-butoxy group, pentyloxy group, hexyloxy group, stearyloxy group, and trifluoromethoxy group; substituted or non-substituted thioalkoxy groups such as methylthio group, ethylthio group, propylthio group, butylthio group, sec-butylthio group, tert-butylthio group, pentylthio group, hexylthio group, heptylthio group, and octylthio group; nitro group; cyano group; carbonyl group; carboxyl group; ester group; hydroxyl group; sulfonic group; vinyl group; amino groups having at least one alkyl substituent such as methylamino group, dimethylamino group, ethylamino group, diethylamino group, dipropylamino group, and dibutylamino group; amino groups having at least one carbocyclic aromatic substituent such as diphenylamino group and ditolylamino group; amino groups having one or two of other substituents such as bis(acetooxymethyl)amino group, bis(acetooxyethyl)amino group, bis(acetooxypropyl)amino group, bis(acetooxybutyl)amino group, and dibenzylamino group; substituted or non-substituted aryloxy groups such as phenoxy group, p-tert-butylphenoxy group, and 3-fluorophenoxy group; substituted or non-substituted arylthio groups such as phenylthio group and 3-fluorophenylthio group; substituted or non-substituted aromatic ring groups such as phenyl group, biphenyl group, triphenyl group, tetraphenyl group, 3-nitrophenyl group, 4-methylthiophenyl group, 3,5-dicyanophenyl group, o-, m-, and p-tolyl group, xylyl group, o-, m-, and p-cumenyl group, mesityl group, pentalenyl group, indenyl group, naphthyl group, azulenyl group, heptalenyl group, acenaphthylenyl group, phenalenyl group, fluolenyl group, antholyl group, anthraquinonyl group, 3-methylantholyl group, phenantholyl group, triphenylene group, pyrenyl group, chrysenyl group, 2-ethyl-1-chrysenyl group, picenyl group, perylenyl group, 6-chloroperylenyl group, pentaphenyl group, pentasenyl group, tetraphenylene group, hexaphenyl group, hexasenyl group, rubisenyl group, coronenyl group, trinaphthylenyl group, heptaphenyl group, heptasenyl group, pyrantrenyl group, and obalenyl group.

It is preferable that the metallic atom in the metal phthalocyanine and the metal phthalocyanine derivative is at least one of iron, cobalt, nickel, palladium, tin, platinum, chromium, manganese, copper, zinc, lead, and rare earth elements. Rare earth elements include scandium, yttrium, lanthanum, cerium, praseodymium, neodymium, promethium, samarium, europium, gadolinium, terbium, dysprosium, holmium, erbium, thulium, ytterbium, and lutetium.

In the present invention, it is more preferable that the phthalocyanine compound is one of iron phthalocyanine, cobalt phthalocyanine, nickel phthalocyanine, tin phthalocyanine, metal-free phthalocyanine, and is a derivative in which one to eight hydrogen atom(s) in the benzene ring of these phthalocyanine molecules is substituted by a halogen atom, an alkyl group having 1 to 6 carbon atoms, a nitro group, a cyano group, a hydroxyl group, or a sulfonic group.

One of the phthalocyanine compounds may be used, or alternatively, two or more of the phthalocyanine compounds may be used in combination.

In the present invention, it is preferable that the phthalocyanine compound is finely powdered so as to be mixed easily and uniformly with the concrete or mortar. Further, the average particle diameter of the fine powder of the phthalocyanine compound is preferably 0.001 μm to 1 mm and more preferably 0.01 μm to 0.1 mm.

In addition to the phthalocyanine compound, the deterioration inhibitor for concrete or mortar of the present invention can contain a known blending agent for concrete or mortar. Such blending agent may be, for example, an AE agent/water reducing agent or a high-performance AE water reducing agent which are used for improving the workability such as fluidity or the like, or an agent for increasing viscosity which is used for preventing the separation of materials.

The AE agent, water reducing agent and the high-performance AE water reducing agent may be a high polymer such as naphthalenes, polycarboxylic acids, melamines, aminosulfonic acids, or the like. Further, the agent for increasing viscosity may be a polysaccharide such as starch, guar gum, methylcellulose, carboxymethylcellulose, xanthan gum, curdlan, or the like or derivatives thereof, or a synthetic high polymer such as polyacrylamide, sodium polyacrylate, polyvinyl alcohol, or the like.

When the deterioration inhibitor for concrete or mortar of the present invention includes a blending agent, the amount of the phthalocyanine compound added to the blending agent is based on the amount of the blending agent added to the concrete or mortar. The added amount of the phthalocyanine compound is preferably 5 to 500 parts by weight, more preferably 10 to 100 parts by weight, based on 100 parts by weight of the blending agent.

When the deterioration inhibitor for concrete or mortar of the present invention includes a blending agent, it is preferable that the phthalocyanine compound is dispersed in the blending agent. In order to disperse the phthalocyanine compound in the blending agent, various types of known grinders or dispersers can be used. More specifically, a three-roll mill or a two-roll mill which disperses the compound by shearing stress; a ball mill, an attriter, a sand mill, a cobol mill, a basket mill, an oscillating mill, or a paint conditioner which disperses the compound by impact force due to the collision with media such as glass beads, zirconia beads, an agate ball, or the like; a disperser, a homogenizer, or a creamix (R) which disperses the compound by rotational blades which generate shearing force, cavitation, collision force, potential core, or the like can be used. Further, a kneader, an extruder, a jet mill, an ultrasonic disperser, or the like can be used.

In the deterioration inhibitor for concrete or mortar of the present invention, the amount of the phthalocyanine compound added is preferably 0.001 to 30 parts by weight, more preferably 0.01 to 5 parts by weight, based on 100 parts by weight of the cement component in the concrete or mortar. When the added amount of the phthalocyanine compound is less than 0.001 parts by weight, it is difficult to sustain the effect of inhibiting and/or killing sulfur oxidizing bacteria over a long time. On the other hand, when the added amount of the phthalocyanine compound exceeds 30 parts by weight, it is not preferable since improvement of the sulfur oxidizing bacteria inhibiting and/or killing effect cannot be expected any more and the cost of implementing the method of inhibiting the deterioration of concrete is high. Further, the strength of the concrete or mortar is greatly reduced.

EXAMPLES

The present invention will be described in detail hereinafter in accordance with Examples and Comparative Examples. However, the present invention is not limited to these.

Examples 1 to 22

2.5 parts by weight of each of the phthalocyanine compounds shown in Table 1 and having an average particle diameter of 1.0 μm was added to a mortar component formed of 100 parts by weight of cement, 200 parts by weight of sand, and 50 parts by weight of water and was kneaded fully with the mortar component by using a mortar mixer. The mixture was placed in a mold and molded, and thereafter, was cured for 28 days (24 hours in a moist box and 27 days in water). A mortar specimen was thereby obtained.

Examples 23 to 44

3.0 parts by weight of each of the phthalocyanine compounds shown in Table 1 and having an average particle diameter of 1.0 μm was added to a concrete component formed of 120 parts by weight of cement and 80 parts by weight of water and was kneaded fully with the concrete component by using a concrete mixer. The mixture was placed in a mold and molded, and thereafter, was cured for 28 days (24 hours in a moist box and 27 days in water). A concrete specimen was thereby obtained.

Examples 45 to 58

0.1 parts by weight of each of the phthalocyanine compounds shown in Table 1 and having an average particle diameter of 1.0 μm was added to a mortar component formed of 100 parts by weight of cement, 200 parts by weight of sand, and 50 parts by weight of water and was kneaded fully with the concrete component by using a mortar mixer. The mixture was placed in a mold and molded, and thereafter, was cured for 28 days (24 hours in a moist box and 27 days in water). A mortar specimen was thereby obtained.

TABLE 1

| Example No. | Phthalocyanine compound | Example No. | Phthalocyanine compound |
| --- | --- | --- | --- |
| 1, 23 | CrPc | 12, 34, 48 | $H_2Pc$ |
| 2, 24 | MnPc | 13, 35, 49 | $NiPc\text{—}Cl_4$ |
| 3, 25 | FePc | 14, 36, 50 | $NiPc\text{-}(t\text{-}Bu)_4$ |
| 4, 26, 45 | CoPc | 15, 37, 51 | $NiPc\text{—}(CN)_4$ |
| 5, 27, 46 | NiPc | 16, 38, 52 | $NiPc\text{—}(NO_2)_4$ |
| 6, 28 | CuPc | 17, 39, 53 | $NiPc\text{—}(CN)_8$ |
| 7, 29 | ZnPc | 18, 40, 54 | $H_2Pc\text{—}Cl_4$ |
| 8, 30 | PdPc | 19, 41, 55 | $H_2Pc\text{-}(t\text{-}Bu)_4$ |
| 9, 31, 47 | SnPc | 20, 42, 56 | $H_2Pc\text{—}(CN)_4$ |
| 10, 32 | PtPc | 21, 43, 57 | $H_2Pc\text{—}(NO_2)_4$ |
| 11, 33 | PbPc | 22, 44, 58 | $H_2Pc\text{—}(CN)_8$ |

In Table 1, CrPc, MnPc, FePc, CoPc, NiPc, CuPc, ZnPc, PdPc, SnPc, PtPc, and PbPc denote metal phthalocyanines whose metal atoms are respectively chromium, manganese, iron, cobalt, nickel, copper, zinc, palladium, tin, platinum, and lead, and $H_2Pc$ denotes a metal-free phthalocyanine. Further, Cl, t-Bu, CN, and $NO_2$ denote substituent atoms or substituents, i.e., chlorine atom, tert-butyl group, cyano group, and nitro group, respectively.

Comparative Example 1

A mortar specimen was obtained using a method similar to that of Example 1 except that a phthalocyanine compound was not added to the mortar specimen.

Comparative Example 2

A mortar specimen was obtained using a method similar to that of Example 1 except that an organic nitrogen sulfur antibacterial agent ("FINE SAND A-3" manufactured by Tokyo Fine Chemical Co.) was added to the mortar specimen instead of a phthalocyanine compound.

Comparative Example 3

A concrete specimen was obtained using a method similar to that of Example 23 except that a phthalocyanine compound was not added to the concrete specimen.

Comparative Example 4

A concrete specimen was obtained using a method similar to that of Example 23 except that an organic nitrogen sulfur antibacterial agent ("FINE SAND A-3" manufactured by Tokyo Fine Chemical Co.) was added to the concrete specimen instead of a phthalocyanine compound.

The specimens obtained in the Examples and Comparative Examples were exposed to sludge on the walls of a sludge facility of a sewage disposal plant for nine months. The extent of adhesion of sulfur oxidizing bacteria and the extent of plastering of the specimen were evaluated as follows. The results are shown in Tables 2 to 4. (Extent of Adhesion of Sulfur Oxidizing Bacteria)

The surface of the specimen was washed by 50 ml of sterilized water (sterilized for 20 minutes in an autoclave) with a toothbrush. The washing solution was treated by ultrasonication, and thereafter, was diluted. The solution was cultured at a temperature of 30° C. for 11 days by using an ONM solid medium to which yeast extract was added and which was set by gellan gum (Imai, Watami, Katagiri, "Growing Conditions of Bacteria by Biochemical Research (Second Report) on Sulfur Oxidizing Bacteria", FERMENTATION INDUSTRY, Vol. 42, page 762, 1964). Then, the number of growth colonies was counted. The number of sulfur oxidizing bacteria per 1 ml of washing solution (cell/ml) was obtained from this value, and the extent of adhesion of the sulfur oxidizing bacteria was evaluated on the basis of the evaluation criteria described below.

Evaluation criteria for extent of adhesion of sulfur oxidizing bacteria

Evaluation 1: $10^6$ cell/ml or more

Evaluation 2: $10^4$ to $10^6$ cell/ml

Evaluation 3: $10^2$ to $10^4$ cell/ml

Evaluation 4: less than $10^2$ cell/ml

Evaluation 5: no adhesion was detected

Extent of Plastering 10 gram of the surface of the specimen was sampled and the amount of calcium sulfate was measured using an X-ray diffractometer. The ratio (%) of calcium sulfate, which is a corrosion product of calcium by sulfate, to calcium in the surface of the specimen was obtained from this value, and the extent of plastering of the specimen was evaluated on the basis of the evaluation criteria described below.

Evaluation criteria for extent of plastering of the specimen

Evaluation 1: 80% or more

Evaluation 2: 50 to 80%

Evaluation 3: 30 to 50%

Evaluation 4: 1 to 30%

Evaluation 5: no plastering was detected

TABLE 2

|  | Extent of Adhesion of Sulfur Oxidizing Bacteria | Extent of Plastering |
|---|---|---|
| Example 1 | Evaluation 5 | Evaluation 5 |
| Example 2 | Evaluation 4 | Evaluation 4 |
| Example 3 | Evaluation 4 | Evaluation 4 |
| Example 4 | Evaluation 4 | Evaluation 5 |
| Example 5 | Evaluation 5 | Evaluation 5 |
| Example 6 | Evaluation 4 | Evaluation 4 |
| Example 7 | Evaluation 4 | Evaluation 5 |
| Example 8 | Evaluation 4 | Evaluation 5 |
| Example 9 | Evaluation 5 | Evaluation 5 |
| Example 10 | Evaluation 4 | Evaluation 5 |
| Example 11 | Evaluation 5 | Evaluation 5 |
| Example 12 | Evaluation 4 | Evaluation 4 |
| Example 13 | Evaluation 5 | Evaluation 5 |
| Example 14 | Evaluation 4 | Evaluation 5 |
| Example 15 | Evaluation 5 | Evaluation 5 |
| Example 16 | Evaluation 4 | Evaluation 5 |
| Example 17 | Evaluation 5 | Evaluation 5 |
| Example 18 | Evaluation 5 | Evaluation 5 |
| Example 19 | Evaluation 4 | Evaluation 5 |
| Example 20 | Evaluation 5 | Evaluation 5 |
| Example 21 | Evaluation 4 | Evaluation 5 |

TABLE 3

|  | Extent of Adhesion of Sulfur Oxidizing Bacteria | Extent of Plastering |
|---|---|---|
| Example 22 | Evaluation 5 | Evaluation 5 |
| Example 23 | Evaluation 5 | Evaluation 5 |
| Example 24 | Evaluation 4 | Evaluation 5 |
| Example 25 | Evaluation 4 | Evaluation 5 |
| Example 26 | Evaluation 5 | Evaluation 5 |
| Example 27 | Evaluation 5 | Evaluation 5 |
| Example 28 | Evaluation 4 | Evaluation 4 |
| Example 29 | Evaluation 5 | Evaluation 5 |
| Example 30 | Evaluation 5 | Evaluation 5 |
| Example 31 | Evaluation 5 | Evaluation 5 |
| Example 32 | Evaluation 5 | Evaluation 5 |
| Example 33 | Evaluation 5 | Evaluation 5 |
| Example 34 | Evaluation 4 | Evaluation 4 |
| Example 35 | Evaluation 4 | Evaluation 5 |
| Example 36 | Evaluation 5 | Evaluation 5 |
| Example 37 | Evaluation 5 | Evaluation 5 |
| Example 38 | Evaluation 5 | Evaluation 5 |
| Example 39 | Evaluation 5 | Evaluation 5 |
| Example 40 | Evaluation 4 | Evaluation 5 |
| Example 41 | Evaluation 4 | Evaluation 4 |
| Example 42 | Evaluation 5 | Evaluation 5 |
| Example 43 | Evaluation 4 | Evaluation 4 |

TABLE 4

|  | Extent of Adhesion of Sulfur Oxidizing Bacteria | Extent of Plastering |
|---|---|---|
| Example 44 | Evaluation 5 | Evaluation 5 |
| Example 45 | Evaluation 4 | Evaluation 5 |

TABLE 4-continued

| | Extent of Adhesion of Sulfur Oxidizing Bacteria | Extent of Plastering |
|---|---|---|
| Example 46 | Evaluation 5 | Evaluation 5 |
| Example 47 | Evaluation 5 | Evaluation 5 |
| Example 48 | Evaluation 4 | Evaluation 4 |
| Example 49 | Evaluation 5 | Evaluation 5 |
| Example 50 | Evaluation 4 | Evaluation 5 |
| Example 51 | Evaluation 5 | Evaluation 5 |
| Example 52 | Evaluation 4 | Evaluation 5 |
| Example 53 | Evaluation 5 | Evaluation 5 |
| Example 54 | Evaluation 5 | Evaluation 5 |
| Example 55 | Evaluation 4 | Evaluation 5 |
| Example 56 | Evaluation 5 | Evaluation 5 |
| Example 57 | Evaluation 4 | Evaluation 5 |
| Example 58 | Evaluation 5 | Evaluation 5 |
| Comparative Example 1 | Evaluation 1 | Evaluation 1 |
| Comparative Example 2 | Evaluation 1 | Evaluation 1 |
| Comparative Example 3 | Evaluation 1 | Evaluation 1 |
| Comparative Example 4 | Evaluation 1 | Evaluation 2 |

In the specimen which contains the phthalocyanine compound of the present invention, the evaluations of the extent of adhesion of the sulfur oxidizing bacteria and the extent of plastering are 4 and 5. However, in the specimen which does not contain the phthalocyanine compound and the specimen which contains the organic nitrogen sulfur antibacterial agent instead of the phthalocyanine compound, the adhesion of sulfur oxidizing bacteria to the specimen is marked, the surface of the specimen is plastered, and the specimen is deteriorated.

As a result, it is found that the phthalocyanine compound of the present invention is effective against the deterioration of concrete or mortar by sulfur oxidizing bacteria.

Industrial Applicability

In the deterioration inhibitor for concrete or mortar and the method of inhibiting the deterioration of concrete or mortar of the present invention, water is not polluted and a small amount of inhibitor can prevent the deterioration of concrete or mortar due to sulfur oxidizing bacteria for a long time. Therefore, the inhibitor and the method can be used for wide applications such as various structures in which concrete or mortar is used.

What is claimed is:

1. A deterioration inhibitor for concrete or mortar comprising a phthalocyanine compound and a blending agent for concrete or mortar, said blending agent selected from the group consisting of an air entraining agent, a water reducing agent, and a viscosity increasing agent, said phthalocyanine compound being present in an amount of 5 to 500 parts by weight based on 100 parts by weight of said blending agent.

2. A deterioration inhibitor for concrete or mortar according to claim 1, wherein the phthalocyanine compound is a metal phthalocyanine and/or a metal phthalocyanine derivative.

3. A deterioration inhibitor for concrete or mortar according to claim 2, wherein the metal atom of the metal phthalocyanine and/or metal phthalocyanine derivative is selected from the group consisting of iron, cobalt, nickel, palladium, tin and platinum.

4. A deterioration inhibitor for concrete or mortar according to claim 2, wherein the metal atom of the metal phthalocyanine and/or metal phthalocyanine derivative is selected from the group consisting of manganese, copper, zinc and lead.

5. A deterioration inhibitor for concrete or mortar according to claim 2, wherein the metal atom of the metal phthalocyanine and/or metal phthalocyanine derivative is a rare earth element.

6. A deterioration inhibitor for concrete or mortar according to claim 1, wherein the phthalocyanine compound is a metal-free phthalocyanine and/or a metal-free phthalocyanine derivative.

7. A deterioration inhibitor for concrete or mortar according to claim 2, wherein the metal phthalocyanine and/or metal phthalocyanine derivative contains a moiety selected from the group consisting of chloro, t-butyl, cyano, and nitro.

8. A method of inhibiting the deterioration of concrete or mortar comprising adding to concrete or mortar a deterioration-inhibiting effective amount of a phthalocyanine compound, said phthalocyanine compound being selected from the group of consisting of a metal phthalocyanine, a metal phthalocyanine derivative, a metal-free phthalocyanine and a metal-free phthalocyanine derivative, the metal atom of said metal phthalocyanine and/or said metal phthalocyanine derivative being selected from the group consisting of chromium, manganese, copper, zinc, lead and a rare earth element.

9. A method of inhibiting the deterioration of concrete or mortar according to claim 8, wherein said phthalocyanine compound is present in an amount of 0.001 to 30 parts by weight per 100 parts by weight of a cement component contained in the concrete or mortar.

10. A method of inhibiting the deterioration of concrete or mortar according to claim 8, further comprising adding a blending agent for concrete or mortar to the concrete or mortar, said blending agent selected from the group consisting of an air entraining agent, a water reducing agent, and a viscosity increasing agent, said phthalocyanine compound being present in an amount of 5 to 500 parts by weight based on 100 parts by weight of said blending agent.

11. A method of inhibiting the growth of sulfur oxidizing bacteria on a surface of a concrete or mortar comprising adding to concrete or mortar a phthalocyanine compound in an amount of 0.001 to 30 parts by weight based on 100 parts by weight of a cement component contained in said concrete or mortar, said phthalocyanine compound being selected from the group consisting of a metal phthalocyanine and a metal phthalocyanine derivative whose metal atom is selected from the group consisting of iron, cobalt, nickel, palladium, tin and platinum.

12. A method inhibiting the deterioration of concrete or mortar according to claim 11, further comprising adding a blending agent for concrete or mortar to the concrete or mortar, said blending agent selected from the group consisting of an air entraining agent, a water reducing agent, and a viscosity increasing agent, said phthalocyanine compound being present in an amount of 5 to 500 parts by weight based on 100 parts by weight of said blending agent.

* * * * *